United States Patent
Atkinson et al.

(10) Patent No.: US 9,839,561 B2
(45) Date of Patent: Dec. 12, 2017

(54) HEMOSTATIC GLOVE DEVICE AND METHOD FOR USE OF SAME

(71) Applicant: INNOVATIVE TRAUMA CARE INC., Edmonton (CA)

(72) Inventors: Ian Atkinson, Cochrane (CA); Dennis Filips, Ottawa (CA); Prasanna Lakshminarasimhan, Edmonton (CA); Steve Dralle, San Antonio, TX (US); Kelly Mottet, Edmonton (CA)

(73) Assignee: Innovative Trauma Care, Inc., Edmonton (CA)

( * ) Notice: Subject to any disclaimer, the term of this patent is extended or adjusted under 35 U.S.C. 154(b) by 269 days.

(21) Appl. No.: 14/103,694

(22) Filed: Dec. 11, 2013

(65) Prior Publication Data

US 2014/0163484 A1    Jun. 12, 2014

Related U.S. Application Data

(60) Provisional application No. 61/735,897, filed on Dec. 11, 2012.

(51) Int. Cl.
| | | |
|---|---|---|
| *A61F 13/00* | (2006.01) | |
| *A61F 13/10* | (2006.01) | |
| *A61F 13/84* | (2006.01) | |

(52) U.S. Cl.
CPC ............ *A61F 13/104* (2013.01); *A61F 13/84* (2013.01); *A61F 2013/00463* (2013.01)

(58) Field of Classification Search
CPC .................... A61F 13/104; A61F 2013/00463
See application file for complete search history.

(56) References Cited

U.S. PATENT DOCUMENTS

| | | | | |
|---|---|---|---|---|
| 4,657,802 A | * | 4/1987 | Morman | ................ D04H 1/565 156/163 |
| 4,720,415 A | * | 1/1988 | Vander Wielen | ......... B32B 5/04 156/163 |
| 5,376,430 A | * | 12/1994 | Swenson | ........... A61F 13/49015 428/152 |
| 5,614,202 A | * | 3/1997 | DeFina | .............. A41D 19/0055 424/400 |
| 5,766,248 A | * | 6/1998 | Donovan | ............... A61B 19/04 2/161.7 |
| 2006/0143767 A1 | * | 7/2006 | Yang | .................... A41D 19/015 2/16 |

(Continued)

FOREIGN PATENT DOCUMENTS

| | | |
|---|---|---|
| CA | 2 545 070 A1 | 7/2005 |
| CA | 2689 472 A1 | 1/2010 |

(Continued)

OTHER PUBLICATIONS

International Search Report regarding PCT/IB2013/003165.
Supplementary European Search Report dated Jul. 25, 2016, regarding EP 13 86 1640.

*Primary Examiner* — Susan Su
(74) *Attorney, Agent, or Firm* — DLA Piper LLP (US)

(57) ABSTRACT

The present disclosure provides a hemostatic glove device including an absorbent fabric layer having a hemostatic agent and optionally an therapeutic agent. The present disclosure also provides methods for using the hemostatic glove device for promoting hemostasis of a wound of a patient.

9 Claims, 2 Drawing Sheets

(56) References Cited

U.S. PATENT DOCUMENTS

| | | | |
|---|---|---|---|
| 2006/0211965 A1* | 9/2006 | Horn | A61F 13/0273 602/13 |
| 2007/0048356 A1* | 3/2007 | Schorr | A01N 47/44 424/443 |
| 2007/0134303 A1* | 6/2007 | Yahiaoui | A61B 19/04 424/443 |
| 2011/0152807 A1* | 6/2011 | Huang | A47L 13/18 604/365 |
| 2012/0004636 A1 | 1/2012 | Lo | |
| 2013/0096515 A1* | 4/2013 | Montrose | A61K 8/31 604/290 |
| 2013/0123213 A1* | 5/2013 | Ji | A61K 31/718 514/55 |
| 2013/0253462 A1* | 9/2013 | Robson | A61F 13/104 604/385.03 |
| 2014/0005616 A1* | 1/2014 | Moreland | A61L 15/44 604/292 |

FOREIGN PATENT DOCUMENTS

| | | |
|---|---|---|
| CN | 2 482 391 Y | 3/2002 |
| WO | WO 2006/065854 A2 | 6/2006 |

\* cited by examiner

HEMOSTATIC GLOVE DEVICE AND METHOD FOR USE OF SAME

CROSS REFERENCE TO RELATED APPLICATION(S)

This application claims the benefit under 35 USC §119(e) to U.S. Application Ser. No. 61/735,897 filed Dec. 11, 2012. The disclosure of each of the prior applications is considered part of and is incorporated by reference in the disclosure of this application.

FIELD OF THE INVENTION

The present invention relates to medical devices for hemostasis. In particular, the invention relates to hemostatic gloves and methods of use thereof.

BACKGROUND

Rapid control of severe bleeding at wound sites is of critical importance in saving lives. Blood loss due to uncontrolled hemorrhage is a major contribution to combat and civilian trauma death before reaching definitive care such as a hospital. Improvements in the ability to control heavy bleeding in the pre-hospital will vastly improve the survival outcomes of trauma. Severe wounds can often be inflicted in remote areas or in situations, such as on a battlefield, where adequate medical assistance is not immediately available. In these instances, it is important to stop bleeding long enough to allow the injured patient (person or animal) to receive medical attention.

Several approaches to date have been used to rapidly stop bleeding in a pre-hospital setting. The most common approach is to provide manual pressure to compress the damaged blood vessel for an indefinite period of time until bleeding stops or transport to definitive care. This is quite difficult not only because of the high blood flow under pressure from a severe wound such as from an artery, but also because it requires knowledge of anatomy to locate the exact site of bleeding and the location where manual pressure will staunch blood flow (the vessel may be deep or the vessel may have retracted). Unless the patient is able to provide self-treatment, manual pressure can be considered to be impractical in many emergency situations due to the need of having one skilled person remain close to the patient to exert continuous pressure, which prevents the care provider from performing other critical life saving functions. Furthermore, heavy direct compression may aggravate damage to other wounded tissues such as fractures, and is inconvenient to apply over irregularly shaped or sensitive body parts. With this approach, it can take a long time to form a stable clot at the injured vessel due to high blood volumes, even when pressed firmly The gold standard in a hospital is the use of sutures, staples, cautery, tissue glues and adhesives by surgical personnel. Appropriate in a hospital setting, these are generally unfit for use in the field. The disadvantage of these closure methods in a pre-hospital setting is that they are required to be performed by an expert in a controlled environment, and take a significant length of time to apply. By example, cyanoacrylate glue's inability to bind to wet surfaces make topical adhesives of this nature inappropriate for use managing arterial bleeding in the pre-hospital. Severe wounds can often be inflicted in remote areas or in situations, such as in a rural setting, where adequate medical assistance is not immediately available. In these instances, it is important to stop bleeding, even in less severe wounds, long enough to allow the injured person (or animal) to receive definitive care at a site such as a hospital.

An alternative to manual pressure is the use of a tourniquet. While utilization of strap style tourniquets have been widely accepted for military field care for centuries, these devices present a number of disadvantages. They must be applied with sufficient constricting force to cause ischemia distal of the site of application. The induced ischemia is both exceedingly painful to the victim and is a common cause of soft tissue and neurological damage to these body parts if left on too long. Tourniquets are slow and difficult to maneuver and place around the extremity. They are limited in its application by how proximal they can be placed on a limb and do not address major junctional bleeding in the groin or axilla (where larger blood vessels run) or other areas of the body (trunk, neck, scalp, etc).

Packing wounds with conventional field dressings have been used for centuries by military and civilian trauma personnel to slow or stop bleeding. Pressure on the wound immediately at the point of injury with pressure dressings and/or packed field dressings can minimize bleeding by distributing pressure evenly over the wound to achieve hemostasis, as well as by decreasing dead space into which blood can accumulate. Multilayered woven and non-woven fabric or all-purpose wound pads, such as gauze pads of various forms of cotton and other cellulose-type material, absorb significant volumes of blood, and act like a sponge. Although these materials have been shown to be the standard of care, they can be slow to unroll and apply when it is unsafe to do so (e.g. dangerous situations such as when under fire); it is difficult to unroll these materials and pack the wound while maintaining constant manual pressure directly on the vessel since the changing of hands is necessary for unrolling and insertion of each length of bandage into the wound; and these materials do not accelerate the patient's ability to clot beyond the natural clotting mechanism.

As a result, there is an increased tendency for absorbent dressings to become saturated with blood due to unstemmed bleeding. It takes anatomical knowledge to know where to pack the dressings and where to hold pressure onto the vessel. It takes significant time to administer, and are cumbersome in rolls or z-folds requiring a technical knowledge to maintain as constant a pressure as possible on the bleeding vessel.

Additionally, or alternatively, several blood clotting materials are generally known, and are typically in the form of a powder or a fine particulate in which the surface area of the material concentrates clotting factors and leads to hemostasis. Undesirable side effects can occur, as the powders can produce an exothermic reaction upon the application of the material to blood. Oftentimes excess material is unnecessarily poured onto a wound, which can exacerbate the exothermic effects. Depending upon the specific attributes of the material, the resulting exothermia may be sufficient to cause discomfort to or even burn the patient; they can also lead to migration of the powder into the vasculature risking clots/emboli away from the wound site.

To avoid the previous disadvantages, hemostatic dressings have become a method of choice, for insertion into wounds to accelerate the clotting process in situ. By dispersing an adsorbed biocompatible polymer throughout the dressing, the dressing acts as a scaffold to initiate clotting and increase clot adhesion to bandage fiber surfaces at the wound site. Several hemostatic dressings have been developed that accelerate the production of a stable clot through the clotting cascade. One example includes dressings that contain a high concentration of human clotting factors. Another example includes gauze bandages (wound in a roll or cut into sheets) impregnated with mineral agents causing water absorption from the blood to the mineral to concentrate clotting factors. Another example includes gauze bandages (wound in a roll or cut into sheets) impregnated with thrombogenic polysaccharide polymer capable of attracting negatively charged blood cells to the bandage to inducing clotting.

Hemostatic dressings have several disadvantages. First is cost; many of these agents are proteins in the "clotting chain," such as, fibrinogen, thrombin, Factor VIII and the like. The cost of products made from these products are very high. Second, certain bandages can be of limited use in wet conditions (e.g. clays), since once the bandage gets wet, the active ingredient is unable to concentrate clotting factors, thereby reducing the clotting potential. Third, such dressings are slow to unroll and apply when it is unsafe to do so (e.g. dangerous situations such as when under fire); difficult to unroll and pack the wound while maintaining constant manual pressure directly on the vessel since the changing of hands is necessary for unrolling and insertion of each length of bandage into the wound. Finally, lack of flexibility makes certain bandages difficult to press into wounds without crumbling or breaking.

What is required is a device designed for use in a field environment that can be applied immediately after wounding. A device that addresses these critical aspects of injury care and that will have significant impact on acute events as well as provide an improved outcome late into the time course of treatment and recovery is necessary. It would therefore be advantageous to provide a means of combining the advantages of applying a hemostatic dressing with the simplicity of applying traditional manual pressure via a glove to the wound to reduce blood loss.

Gloves come in many varieties; each designed to protect a person's hand from some sort of hazard without overly impairing the person's manual dexterity. For example, latex gloves protect health care providers such as combat medics and EMT personnel from external contamination while allowing them to handle small, delicate surgical tools, and also prevent the patient from being contaminated by microorganisms on the hands of the health care provider.

Beyond infection control, there are currently no gloves in use that are used/worn by medical personnel to treat patients directly. Bandages that are used by caregivers tend to be in the form of rolls or sheets of woven or non-woven fabric. Gloves that are worn by the caregiver act as a barrier for protection of the caregiver, not for the treatment of the patient by the caregiver.

Bandage gloves are known in the art, and are primarily used for treatment of fingers and hands that can suffer a variety of ailments and injuries such as blisters, arthritis, hand burns, and the like. Examples of such are cloth-like wraps and finger sleeves that have been developed to be placed around an ailing joint to provide warmth and support.

In U.S. Pat. No. 7,767,874 issued to Kellogg et al., a medical glove is provided for removal of excess fluids from body tissue and is particularly useful to treat soft tissue inflammation, damage, edema and/or lymphedema.

In U.S. Pat. No. 5,701,918 issued to Jiraki, provides a glove used in endotracheal intubations having one or more finger extension members attached to and extending outwardly from fingertip portions of one or more finger covers thereof.

In U.S. Pat. No. 5,614,202 issued to DeFina, a moisturizing glove is disclosed in which a middle layer saturated with lotion, an exterior layer of non-porous material, and an inner layer having multiple pores, creates a cavity for receiving and enveloping a hand.

In U.S. Pat. No. 4,853,978 issued to Stockum, an antimicrobial medical glove with an inner coating containing a slow release antimicrobial agent sufficient to maintain an essentially bacteria-free and fungus-free environment within a donned glove.

In U.S. Pat. No. 7,230,153 issued to Flick, a silver bandage (e.g. Silverlon) is formed into a glove and is applied to protect and treat hand burns/wounds from infection.

However, the art fails to describe or suggest a use of gloves to provide external hemostasis treatment, wherein the gloves are worn by the caregiver to treat or provide therapeutic needs. What is desirable is a method to reduce blood loss during/after trauma that mimics the action of manual pressure applied by a first responder, but also mimics the last step of the physiological coagulation mechanism through the use of an adsorbed hemostatic agent to stop bleeding. Furthermore, a device designed for use in a field environment that can be applied immediately to a wound to stop bleeding is desirable.

SUMMARY OF THE INVENTION

The present invention relates to a hemostatic glove device for promoting hemostasis at or within a wound site. The glove device of the present disclosure is designed to accelerate clotting and staunch bleeding concurrent with manually applied pressure at a wound site.

Therefore, in one aspect, the present disclosure provides a hemostatic glove adapted to be worn by a user. The glove includes an absorbent fabric layer having a hemostatic agent impregnated or disposed on the fabric layer. The glove may further include an interior elastomeric layer forming a fluid barrier to protect the user from contact with fluid from the wound site. The absorbent fabric layer is separable from the interior elastomeric layer such the fabric layer may be removed from the user's hand and used to pack the wound.

In another aspect, the present disclosure provides method for promoting hemostasis in a wound of a patient. The method includes (a) contacting the wound with a hemostatic glove of the present invention; and (b) applying manual pressure on or within the wound to limit egress of fluid from the wound, thereby promoting hemostasis in the wound. The method may further include separating the absorbent layer from the elastomeric layer and removing the absorbent layer from the user's hand and using the absorbent layer to pack the wound.

In another aspect, the present disclosure provides a kit. The kit may include a hemostatic glove of the present disclosure and instructions for promoting hemostasis in a wound of a patient using the glove.

BRIEF DESCRIPTION OF THE FIGURES

In the drawings, like elements are assigned like reference numerals. The drawings are not necessarily to scale, with the emphasis instead placed upon the principles of the present invention. Additionally, each of the embodiments depicted are but one of a number of possible arrangements utilizing the fundamental concepts of the present invention. The drawings are briefly described as follows.

DETAILED DESCRIPTION

The invention relates to a hemostatic glove device. When describing the present invention, all terms not defined herein have their common art-recognized meanings. To the extent that the following description is of a specific embodiment or a particular use of the invention, it is intended to be illustrative only, and not limiting of the claimed invention. The following description is intended to cover all alternatives, modifications and equivalents that are included in the spirit and scope of the invention, as defined in the appended claims.

The invention addresses critical aspects of field care, providing point of injury care that will have significant impact on acute events as well as improve outcome late into the time course of treatment and recovery. It is therefore advantageous to provide a means of combining the advantages of applying a hemostatic dressing along with applying a glove to a wound to perform traditional manual pressure to introduce hemostatic agents to reduce blood loss.

To those ends are provided hemostatic products for combat and civilian casualty care. The invention exploits the tendencies of first responders or medics to use manual pressure for immediate care. Most medics quickly grab at an open wound as a first response to apply manual pressure. The present invention is a solution that integrates a medical hemostatic glove which may be adapted to tightly conform over a donned surgical glove or itself include an interior surgical glove.

Light and portable, the glove of the present disclosure is immediately accessible and can be applied over surgical gloves within seconds and subsequently acts as a hemostatic bandage. For example, the hemostatic glove may be used to pack into a wound for contact hemostasis, wherein an absorbent fabric layer of the glove having a hemostasis agent can be removed from the caregiver's hands and temporarily inserted into the wound.

As used herein, "user" or "wearer" refers to a human. As also used herein, a "hand" is the terminal part of the human arm located below the forearm consisting of the wrist, palm, four fingers, and an opposable thumb.

Figure 1:
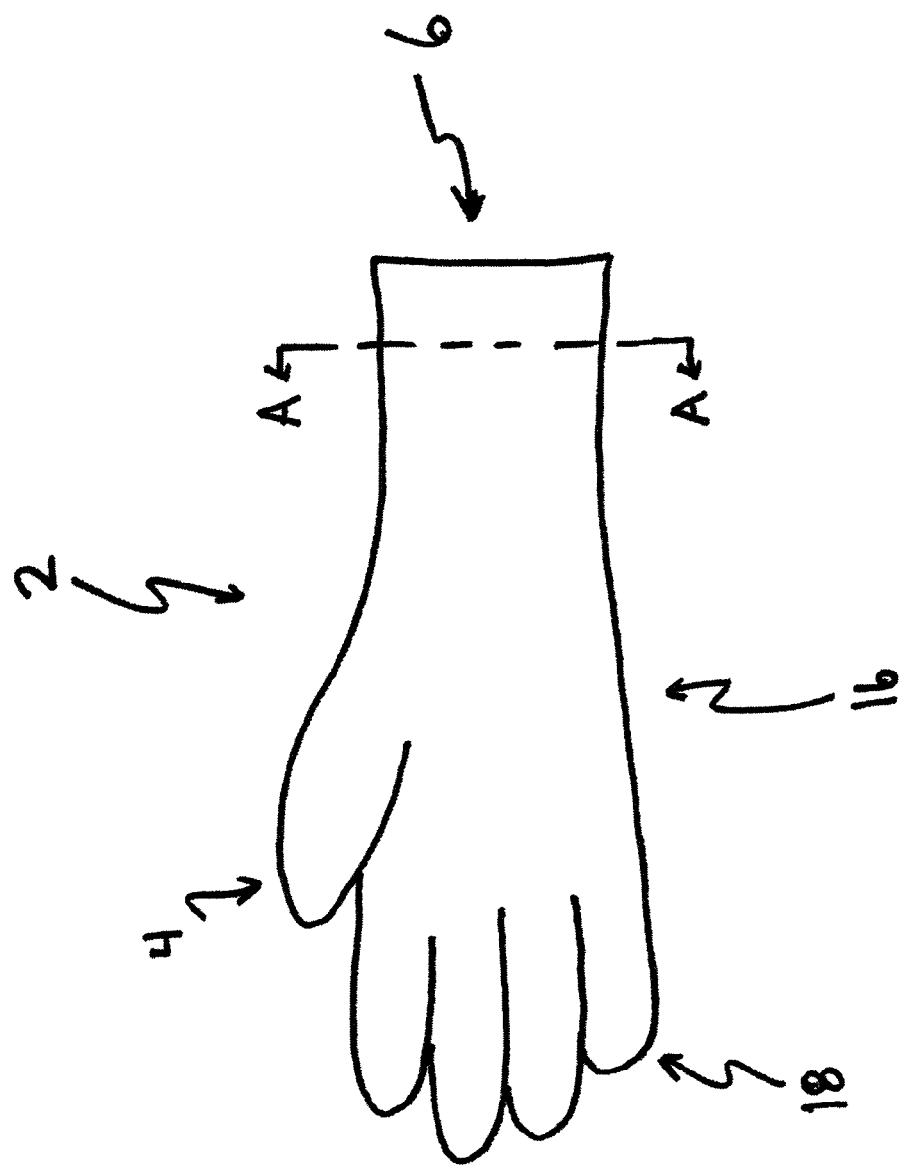
FIG. 1 is a view of a glove in one embodiment of the disclosure.

With reference to FIG. 1, a hemostatic glove (2) of the present invention is illustrated. In at least one embodiment, the medical glove (2) is sized to fit a wearer's hand. The glove (2) has a closed end (4) and an open end (6). The open end (6) of the glove (2) provides an entry point for the wearer's hand. Thus an interior cavity that is sized for the wearer's hand is defined by the inner surface of the glove. The glove (2) can be right handed, left handed, or ambidextrous. The glove (2) can be considered to have two "sides" with one side being adjacent to a palm of the wearer's hand (hereinafter the palm side) and the other side being adjacent to the back of the wearer's hand (hereinafter the back side).

The glove body (16) includes five fingers (18) at the closed end (4) of the glove (2). The five fingers (18) enclose the four fingers and thumb of the wearer's hand. In some embodiments, when the glove (2) is worn by the wearer, the glove body (16) encloses the wearer's hand. In other embodiments, when the glove (2) is worn by the wearer, the glove body (16) encloses the wearer's hand and at least a portion of the wearer's forearm adjacent to the hand.

In general terms, one embodiment of the hemostatic glove is configured with an exterior absorbent fabric layer having a hemostatic agent impregnated or disposed on the fabric layer. In such an embodiment, the glove may be donned as an outer layer over a user's hand already having a surgical glove on it. Alternatively, the hemostatic glove is configured with an interior elastomeric layer which forms a fluid barrier to protect the user from fluid.

Figure 2:
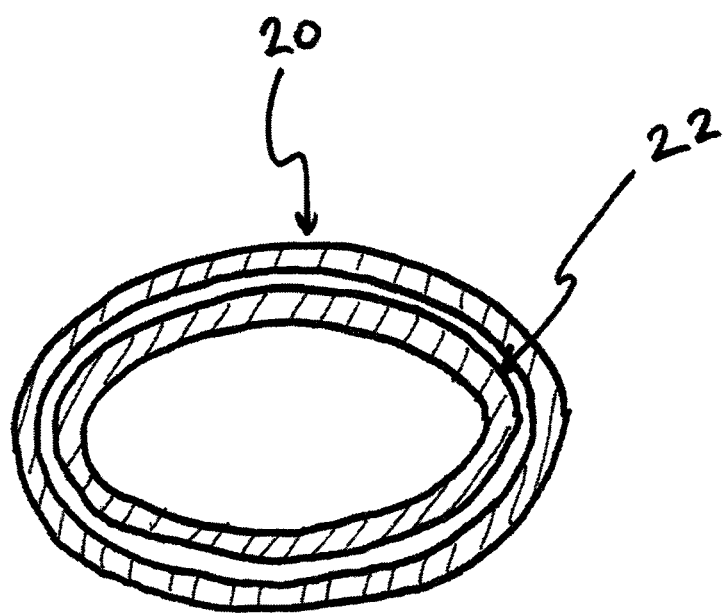
FIG. 2 is a cross-sectional view of a portion of the glove of FIG. 1 at line A-A of FIG. 1.

As shown in FIG. 2, the glove may include an outer absorbent fabric layer (20) having a hemostatic agent which is disposed over an interior elastomeric layer (22). The exterior fabric layer provides for absorption of fluid and hemostasis while the interior elastomeric layer provides a barrier to contact with body fluids thereby preventing exposure to pathogens or other biohazards to preventing transmission of disease or contaminants.

In various embodiments, the elastomeric layer is composed of, but not limited to, latex, rubber, nitrile, neoprene, vinyl, and combinations thereof.

In some embodiments, the absorbent fabric layer is woven, non-woven or a combination thereof. In general, the type of fabric, thickness of the fabric, number of layers, as well as the type of hemostatic agent used may be adjusted as desired for a particular clinical application. It is envisioned that a wide variety of fabrics may be utilized, especially those that are conventionally used to fabricate bandages. Fabric with the following characteristics are envisioned: those of sufficient absorbancy for use on heavily bleeding wounds; those capable of significantly slowing blood flow from the wound site by applied pressure at the wound vessel/dressing interface; those that do not shed fibers nor leach out hemostatic substances into the wound cavity or corresponding vessels; and those that are not chemically unsuitable for use as a first aid dressing, for example those that leave a residue in the wound that needs to be cleaned out after use.

In various embodiments, the fabric may be composed of one or more different types of fibers, including synthetic or naturally derived fibers. By way of illustration, fibers for use in the present invention may include, but are not limited to, glass, such as fiberglass; silk fibers; polyester fibers; nylon fibers; ceramic fibers; polysaccharide fibers including plant fibers such as raw or regenerated (e.g., chemically processed) bamboo, cotton, rayon, linen, ramie, jute, sisal, flax, soybean, corn, hemp, and lyocel; animal fibers such as wool; lactide and/or glycolide polymers; lactide/glycolide copolymers; silicate fibers; polyamide fibers; feldspar fibers; zeolite fibers, zeolite-containing fibers; acetate fibers; plant fibers that have been genetically engineered to express mammalian coagulation proteins or mammalian vasoactive factors. Other fibers that are suitable for use in the present invention are fibers that have been covalently modified with polymers to promote water absorbancy (e.g., polyvinyl alcohols) and polymers that contain molecular moieties that activate hemostatic systems (e.g., linear or cyclized-arginine-glycine-aspartate-moieties such as those found in eptifibatide). In some embodiments, fibers include plant fibers such as raw or regenerated (e.g., chemically processed) bamboo fibers, cotton fibers, and the like, that have high moisture absorbancy and that are capable of activating the intrinsic coagulation cascade. The fibers may be prepared using conventional methods, including ring, open end (OE), rotor, or air jet spinning, and may have counts ranging from 1/1 to 100/1 Ne.

As will be appreciated by one of skill in the art, the fibers may be used singly, or in combinations of two, three, four, or more in a blended or plied state. In addition, any type of combination of fibers may be used. For example, in one embodiment, two or more fibers may be individually produced and then blended or plied together to form a composite yarn. In another embodiment, the fibers may be formed as a conjugate comprising blocks of the selected types of fibers, for example alternating blocks of polyesters and polysaccharides. In yet another embodiment, the fibers may be formed as a homogeneous combination of different threads.

As discussed herein, the absorbent fiber layer includes one or more hemostatic agents which may be impregnated or coat the fiber layer. The hemostatic agent may be applied to the entire layer such that it is disposed over the entire glove, or alternatively be disposed at discrete locations on the fiber layer, for example, on the palm or finger regions. By way of illustration, hemostatic agents that may be used include biological and chemical agents, without limitation, procoagulant enzymes, proteins and peptides, either naturally occurring, recombinant, or synthetic. Some hemostatic agents include, rehydrated lyophilized (RL) platelets, RL blood cells, prothrombin, thrombin, fibrinogen, fibrin, fibronectin, Factor X/Xa, Factor VII/VIIa, Factor IX/IXa, Factor XI/XIa, Factor XII/XIIa, tissue factor, von Willebrand Factor, collagen, elastin, gelatin, synthetic peptides having hemostatic activity, clays, chitosan, polyacrylamides, chemically modified cellulose, derivatives of the above and any combination thereof, other coagulation cofactors such as components of animal venom, such as reptilase, or vasoactive agents such as endothelins, thromboxanes, nitrous oxide (NO) scavengers, or combinations thereof. These factors, or any of the factors listed above, may be in a dry or liquid form when incorporated into the fabric layer of the invention.

The preferred amount of hemostatic agent in the fabric layer of the invention ranges from about 0.01% by weight to about 10% by weight, based on the total weight of the dry fabric layer. For example, amounts of hemostatic agent included in the fabric layer of the invention range from about 0.05% by weight to about 7% by weight, or from about 0.1% by weight to about 5% by weight, all based on the total weight of the dry fabric layer.

As a complement to the hemostasis function of the glove, additional therapeutic agents may be included in the fiber layer of the glove. Such agents include, for example, antifibrinolytics, wound healing agents, antibacterial agents, antimicrobial agents, growth factors, analgesic and anesthetic agents for treatment. Therapeutic agents that may be included in the fabric layer of the invention include skin conditioners such as aloe vera, vitamin E, coenzyme Q, collagen, and the like; anti-inflammatory agents such as aspirin, ibuprofen, acetominophen, vitamin C, COX-2 inhibitors, steroids, and the like; analgesics such as lidocaine, tetrocaine, opiates, cocaine, antihistamines, and the like; antimicrobial or antifungal agents such as bacitracin, silver salts, iodide, and the like; vasoconstrictors such as epinepherine, norepinephrine, vasopressin, hemoglobin, endothelins, thromboxanes, NO scavengers, and the like; growth factors such as MMP inhibitors, PDGF, and the like; anti-scar agents such as IL-11, anti-kheloid compounds, and the like; cauterizing agents that undergo an exothermic reaction upon rehydration such as zeolites; dehydrating agents that are hydroscopic such dextran; prothrombotic agents, such as zeolite, dextran sulfate, polyphosphate, mineral interfaces, phosphatidyl serine, calcium, and the like.

In use, the glove may be rapidly applied, taking only a few seconds to properly position for donning the gloves over the user's hands. Additionally, the fabric layer of the glove must be rapidly separable from the elastomeric layer for insertion into a wound after removal from the user's hand. In some embodiments, the glove includes one or more pull tabs integrated into the fabric layer to assist with one-handed removal of the fabric layer. In some embodiments, the fabric layer and elastomeric layer are releasably coupled to one another via an adhesive, velcro, heat bonding, stitching, or combination thereof.

As discussed herein, the hemostatic glove further provides a method for promoting hemostasis in a wound of a patient. After the caregiver puts a hemostatic glove onto his hand, the wound is contacted with the glove. The caregiver simultaneously applies manual pressure on or within the wound to limit egress of fluid from the wound, thereby promoting hemostasis in the wound. The method may further include separating the absorbent layer from the elastomeric layer and removing the absorbent layer from the user's hand and using the absorbent layer to pack the wound. Additionally, the user may apply a wound clamp to the wound.

To assist in applying manual pressure on the wound, the glove may include grips positioned in the finger and palm region. Such grips may be composed of latex, rubber, plastic or similar material to reduce slippage while applying manual pressure, especially when the device is covered with fluid such as blood.

The following is an illustrative use of the hemostatic glove in which manual pressure and bandage contact is provided at the same time. The user's finger or palm is applied to the external wound surface, the internal wound surface, or the skin edges to seal the affected vessel with manual pressure. When such pressure is applied to stem the blood flow and create a blood clot, there would be a reduction in the speed and amount of fluid egress. It also creates the conditions for a static blood being present in the fabric layer of the glove present in/near the wound, increasing the chance of clotting and strengthening the wound site. If an increase in pressure is required due to an amount of leakage from the wound, an increase in manual pressure from the finger or palm will further reduce flow from the affected vessel and further increase the chance of clotting. Each finger can generate adjustable pressure to keep the vessel closed.

Contemplated herein is application of hemostatic agent to the fiber layer in the finger and palm regions of the glove, by a chemical means so as to keep the hemostatic agent from going into the body of the patient and causing clotting complications. For example, adhered hemostatic agents that do not cause thrombotic complications in the body may be used. Alternatively, a hemostatic agent that is not adhered to the surface of the fabric layer and that does not cause thrombotic complications in the body may be utilized.

Further, it is envisioned that the fiber layer be disposed completely over the hand of the user, or alternatively only over one or more portions of the user's hand, such as a single finger. By way of illustration, a nose bleed may be treated using an embodiment of the device wherein the fabric layer is only disposed over a single finger.

In another aspect, the present disclosure provides a kit. The kit may include a hemostatic glove of the present disclosure and instructions for promoting hemostasis in a wound of a patient using the glove. The kit may further include additional medical devices, such as wound clamps, needles and the like, as well as reagents commonly utilized in medical procedures.

The following examples are provided to further illustrate the advantages and features of the present invention, but are not intended to limit the scope of the invention. While they are typical of those that might be used, other procedures, methodologies, or techniques known to those skilled in the art may alternatively be used.

EXAMPLE 1

Glove Absorption

Absorption capability was shown by introduction of a worn glove device to an amount of fluid in the proximity of a porcine wound and the volume was absorbed. The whole volume was absorbed by the gloved index finger and gloved thumb, showing substantial equivalence to standard gauze pads, and taking the same length of time to absorb an amount of fluid. Evidence of effect was the presence of blood transferred from the skin to the glove. Absorbing capability shown through weight of absorption in the fingers of the glove. The amount collected relative to a similar set up with 4 inch×4 inch gauze pads or rolled gauze pads was equivalent.

Secondly, applying a finger cot with the same wound to a small crevice was convenient and easy. The glove was too large to fit into the wound pocket upon removal, but the finger cot could be removed and packed into the wound before sealing with a wound clamp.

Absorption capability was also shown by introduction of a worn glove device to an amount of fluid in the proximity of a cadaver wound and the volume was absorbed. Sterile water was introduced to the cadaver and pumped (as described by Mottet et al. (Mottet K, Filips D, Logsetty S, Atkinson I. Evaluation of the iTClamp 50 in a Human Cadaver Model of Severe Compressible Bleeding. The Journal of Trauma, Accepted 2013)). The whole volume of sterile water in the wound cavity was absorbed by the gloved index finger, showing substantial equivalence to standard gauze pads, and taking approximately a similar length of time to absorb an amount of fluid. Evidence of effect was the presence of water transferred from the skin and wound to the glove, as well as the weight of the clear fluid to the surface of the glove after finger contact surrounding and into the wound.

EXAMPLE 2

Method Using Wet Gloved Fingers as Retractors

A gauze-gloved finger dampened so as not to stick to the tissue was determined to help to stabilize slippery tissue, such as the tongue. Sterile water was used to moisten the index finger and thumb of the gauze glove. The tongue of a porcine model was grasped with index finger and thumb and manipulated in multiple dimensions. No damage was done to the tissue, and the glove surface did not stick to or tear the tongue tissue.

EXAMPLE 3

Method Using Agent Disposed on Fabric Layer

Where a wound needs to have a fluid solution added to the skin or the wound site, a dry gauze glove or a gauze finger cot is typically used to add and/or remove fluid agent to cut skin or another wound site. Wet active agent was absorbed to the fabric layer of the glove.

Upon drying, a bloody wound site on an anaesthetized porcine model was treated with two fingers of the glove of the invention and the skin wound was irrigated with several milliliters of a 0.15% Chlorhexidine solution via a direct pour of ~10 ml from the bottle. A dry finger of gauze on the prototype glove was used to collect expressed overflow fluid on the skin below the wound. One finger was used to spread the fluid onto a wider area of the skin than was originally covered by pouring. Instead of leaving the solution in the wound for a long period of time as is typical, the solution could be removed after only a few seconds. The palm and back of the glove were used to dry the skin surface volume; the dry fingers (not used to dry the wound of original fluids, nor to collect the overflow solution) were used to absorb the newly introduced solution from the internal wound area. Due to the speed of processing—including not having to take the glove off to get access to dry surfaces for drying the irrigated skin or wound pocket—the process was very timely and efficient.

After treatment as described, fluid spreading across the wound and surrounding skin was clear (blood-free) and excess fluid readily absorbed. If additional fluid volume was present upon saturation of the existing gloved palm or fingers, the thumb could also have been used to aid in its absorption.

A 10% Povidone-iodine solution was used to disinfect the skin of a cadaver model at the location of a surgical incision. The index finger of the woven glove was introduced into the povidone-iodine solution for a few seconds, and then transferred to the skin. With mild pressure the antiseptic solution was squeezed from the finger onto the skin. The finger was moved around onto the skin area to spread the solution across the surface of the skin where the incision was performed. Upon completion, the palm was used to dry the skin and absorb the remaining solution. The absorptive capability shown through the transfer of solution and color to the skin surface combined with the minimal presence of iodine staining of the human skin evidenced substantial equivalence to the function of standard gauze pads for this purpose, but achieved more quickly and conveniently than possible through pressure application of gauze.

An active agent was dried onto the glove's surface and tested for transfer to a wound. Where a wound needs to have a dry agent applied to the skin or the wound site, an active therapeutic agent (e.g., an antibiotic) can be impregnated into the outer surface of the glove of the invention by application as a fluid followed by drying, covalent bonding of the agent with the glove material, application as a dry coating, or by similar means. The active agent is released onto the skin or wound site when contacted with fluid (e.g., blood).

To that end, a saturated solution of aluminum sulfate was created in a 100 ml beaker. A hemostatic glove (gauze/woven fabric layer) was placed "fingers first" into the beaker, and the wrist was wrapped around the opening. Upon allowing time for crystallization to occur, the fingers of the glove developed crystals of several sizes on the fibers. The glove was allowed to dry completely prior to use. Individual fingers of the glove were cut to form finger cots for use. Upon separation of the fabric layers to open the finger cots, the finger cots were ready for insertion onto the hand of the caregiver already wearing a blue nitrile surgical glove.

A bleeding wound was created on an anaesthetized porcine model. Upon allowing the wound to free-bleed for only a few seconds, a finger cot was placed onto the index finger of the surgical glove wearing caregiver, and was inserted into the wound cavity to slow the bleeding. Direct pressure was applied directly to the wounded vessel for 1 minute with the index finger. The finger cot was stripped off the finger, and pressed into the wound cavity, followed by skin closure over the finger cot with a wound closure clamp. No further external blood loss from the wound was observed. After 2 minutes, upon removal of the clamp and the finger cot from the wound, bleeding from the wound site was observed to be slowed.

A wound was also created on the thigh of a cadaver model. 2 finger cots with dried aluminum sulfate were prepared for use. Upon allowing the wound to express sterile water for only a few seconds, both finger cots were applied to the caregiver's hand and the index and third finger were inserted into the wound cavity to slow the fluid flow. Direct pressure was applied directly to the wounded vessel for 1 minute with the 2 fingers. The cots were stripped off the hand, and pressed into the wound cavity, followed by skin closure over the glove with a wound clamp. No further external fluid loss from the wound was observed. Absorptive capability was shown through a weight of fluid absorption into the fabric.

Active agent adsorbed onto the non-woven fabric layer with activated carbon fiber. Where a wound needs to have a dry agent applied to the wound site, but the agent needs to remain with the glove to avoid migration of the active agent for safety reasons, the use of a fabric glove or finger cot with adsorbed agent, as part of the glove surface, is required.

To further demonstrate release of an adsorbed agent from the glove of the invention, a fabric containing adsorbed activated carbon was sewn into the form of a glove to form the hemostatic glove. A small bleeding wound was created on an anaesthetized porcine model. Upon allowing the wound to free-bleed for only a few seconds, the glove was placed onto the hand of the surgical glove wearing caregiver, and was inserted onto the skin at the wound to slow the bleeding. Direct pressure was applied directly to the wounded vessel for 1 minute with the index finger. No further external blood loss from the wound was observed. Absorptive capability was shown through a weight of blood absorption into the fabric.

A similar bleeding wound was created on an anaesthetized porcine model in parallel. The whole glove was prepared for use. Upon allowing the wound to free-bleed for only a few seconds, a glove was applied to the caregiver's hand and two fingers were inserted into the wound cavity to slow the bleeding. Direct pressure was applied directly to the wounded vessel for 1 minute with the index and third finger. The glove was stripped off the hand, and pressed into the wound cavity, followed by skin closure over the glove with a wound clamp. No further external blood loss from the wound was observed. Upon removal of the glove, bleeding from the wound site was observed to be reduced. Absorptive capability was confirmed by measuring the weight of blood absorption into the fabric.

A wound was also created on the thigh of a cadaver model. Finger cots were prepared for use. Upon allowing the wound to express sterile water for only a few seconds, a finger cot was applied to the caregiver's hand and a single index finger was inserted into the wound cavity to slow the fluid flow. Direct pressure was applied directly to the wounded vessel for 1 minute with the index finger. The cot was stripped off the hand, and pressed into the wound cavity, followed by skin closure over the glove with a wound clamp. No further external fluid loss from the wound was observed. Absorptive capability was confirmed by measuring the weight of fluid absorption into the fabric.

Although the invention has been described with reference to the above example, it will be understood that modifications and variations are encompassed within the spirit and scope of the invention. Accordingly, the invention is limited only by the following claims.

What is claimed is:

1. A hemostatic glove adapted to be worn by a user, comprising an exterior absorbent fabric layer having a hemostatic agent, with the proviso that the hemostatic agent is devoid of chitosan, and an interior elastomeric layer forming a fluid barrier, wherein the interior and exterior layers are releasably coupled to one another.

2. The hemostatic glove of claim 1, wherein the absorbent fabric is a woven fabric, non-woven fabric or combination thereof.

3. The hemostatic glove of claim 1, wherein the hemostatic agent is impregnated within the absorbent fabric layer.

4. The hemostatic glove of claim 1, wherein the absorbent fabric layer is coated with the hemostatic agent.

5. The hemostatic glove of claim 1, wherein the absorbent fabric layer further comprises a therapeutic agent.

6. The hemostatic glove of claim 5, wherein the therapeutic agent is selected from the group consisting of wound healing agents, antibacterial agents, antimicrobial agents, growth factors, analgesic agents, and anesthetic agents.

7. The hemostatic glove of claim 1, wherein the hemostatic agent is disposed on or within one or more finger portions of the glove.

8. The hemostatic glove of claim 1, wherein the interior elastomeric layer comprises plastic, latex, rubber, nitrile, neoprene, vinyl, or a combination thereof.

9. A kit comprising the hemostatic glove of claim 1 and instructions for promoting hemostasis in a wound of a patient using the glove.

* * * * *